(12) United States Patent
Yamada et al.

(10) Patent No.: US 7,297,106 B2
(45) Date of Patent: Nov. 20, 2007

(54) MEDICAL TREATING INSTRUMENT

(75) Inventors: Hideo Yamada, Sakura (JP); Eiji Kanehira, Kanazawa (JP); Kiyotaka Arikawa, Akita (JP); Minoru Shibata, Akita (JP); Kei Hara, Akita (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 544 days.

(21) Appl. No.: 10/483,847

(22) PCT Filed: Jul. 16, 2002

(86) PCT No.: PCT/JP02/07220

§ 371 (c)(1),
(2), (4) Date: Jan. 14, 2004

(87) PCT Pub. No.: WO03/007821

PCT Pub. Date: Jan. 30, 2003

(65) Prior Publication Data

US 2004/0173218 A1 Sep. 9, 2004

(30) Foreign Application Priority Data

Jul. 18, 2001 (JP) .............................. 2001-218851
Nov. 2, 2001 (JP) .............................. 2001-337264

(51) Int. Cl.
*A61B 17/02* (2006.01)
(52) U.S. Cl. .................................................. 600/208
(58) Field of Classification Search ................ 600/206, 600/208, 201; 606/213, 215, 216
See application file for complete search history.

(56) References Cited

U.S. PATENT DOCUMENTS

| 5,366,478 A | 11/1994 | Brinkerhoff et al. |
| 5,480,410 A | 1/1996 | Cuschieri et al. |
| 5,514,133 A * | 5/1996 | Golub et al. ................... 606/1 |
| 5,640,977 A | 6/1997 | Leahy et al. |
| 5,653,705 A | 8/1997 | de la Torre et al. |

(Continued)

FOREIGN PATENT DOCUMENTS

JP    Y1-48-12479    4/1973

(Continued)

OTHER PUBLICATIONS

Chinese Office Action Dated 08/26/2005 for the Related Chinese Application.

*Primary Examiner*—Cary E. O'Connor
(74) *Attorney, Agent, or Firm*—Smith, Gambrell & Russell LLP

(57) ABSTRACT

There is provided a surgical treatment instrument in which the mode can be easily switched between a treatment under a pneumoperitoneum condition and a treatment outside the peritoneal cavity, and forceps can be manipulated under the pneumoperitoneum condition, and when taking out a cancer-affected part, an incision in the abdominal wall is protected, and the incision is free from infection. The surgical treatment instrument includes a tubular portion which has a first fixing member provided at a near end-side open portion thereof, and also has a second fixing member provided at a remote end-side open portion thereof. At least two tension belts are mounted on the second fixing member, and fixing means for adjusting the length of the tension belts to position the first fixing member is provided at the first fixing member.

18 Claims, 8 Drawing Sheets

U.S. PATENT DOCUMENTS

| | | |
|---|---|---|
| 5,741,298 A | 4/1998 | MacLeod |
| 5,813,409 A | 9/1998 | Leahy et al. |
| 6,033,426 A | 3/2000 | Kaji |
| 6,846,287 B2 * | 1/2005 | Bonadio et al. ............ 600/208 |
| 2001/0037053 A1 * | 11/2001 | Bonadio et al. ............ 600/208 |
| 2003/0078478 A1 * | 4/2003 | Bonadio et al. ............ 600/208 |
| 2005/0197537 A1 * | 9/2005 | Bonadio et al. ............ 600/208 |
| 2005/0288558 A1 * | 12/2005 | Ewers et al. ................ 600/206 |

FOREIGN PATENT DOCUMENTS

| | | |
|---|---|---|
| JP | 10-108868 | 4/1998 |
| JP | 11-099156 | 4/1999 |
| JP | 11-160942 | 6/1999 |
| WO | WO 98/48724 | 11/1998 |
| WO | WO 00/32116 | 6/2000 |

* cited by examiner

FIG. 5
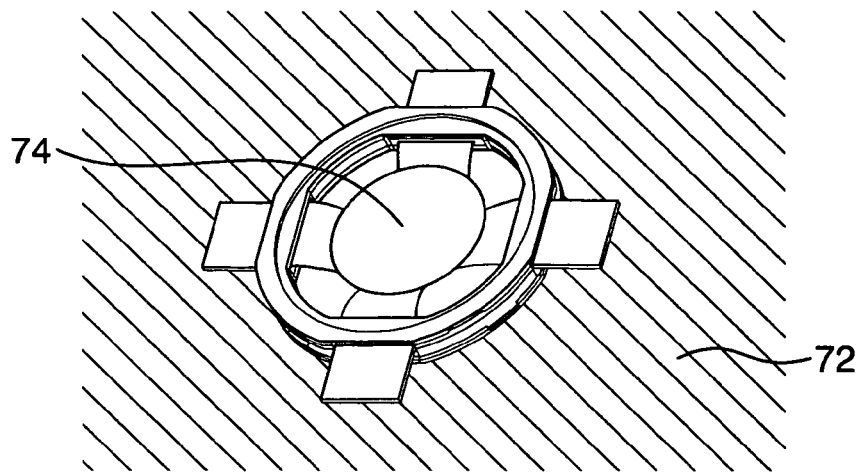
FIG. 6A
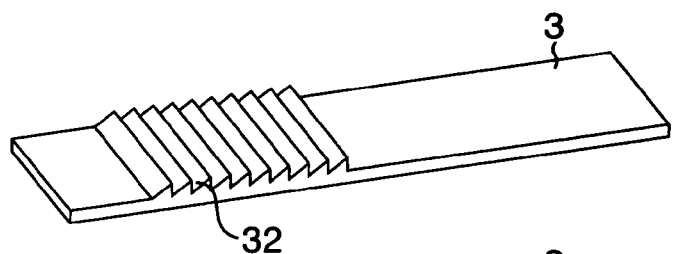
FIG. 6B
FIG. 6C
FIG. 7A
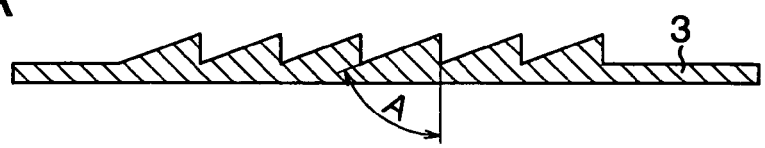
FIG. 7B
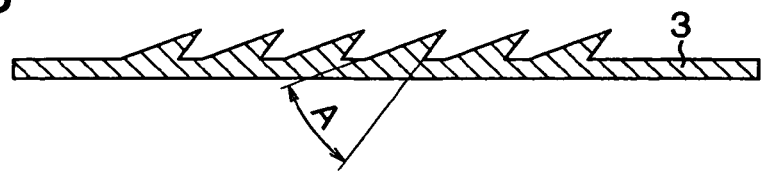

MEDICAL TREATING INSTRUMENT

TECHNICAL FIELD

This invention relates to a surgical treatment instrument for opening an incision. Particularly, the invention relates to a surgical treatment instrument used in the cases where after a treatment is effected under a pneumoperitoneum condition, the pneumoperitoneum condition is canceled, and an internal organ is taken out of the body, and is treated, and where the organ is again returned into the body, and again under a pneumoperitoneum condition, an affected part is confirmed, and also an additional treatment is given.

BACKGROUND ART

In recent years, endoscopic surgical operations have been extensively performed as a low-invasion surgical operation method. The endoscopic surgical operation is a low-invasion operation, and has advantages that the term of hospitalization is short and that a wound is small. On the part of the operator, there are disadvantages that since the operator performs the operation, using treatment instruments, such as a plurality of forceps, while viewing an image projected on a screen by the endoscope, the manipulation is difficult, and much time is required, so that the operator undergoes a considerable stress. Particularly, it tends to take a long time to perform an operation on the stomach and the large intestine, and the operator undergoes a great stress. Therefore, when it is expected that a large sample is finally taken out after a treatment under an endoscope is effected, there is required a surgical treatment instrument capable of easily closing a small incision (on the premise that such a smaller incision is formed) so that the procedure can easily shifted from the treatment under the pneumoperitoneum condition to the treatment applied to the internal organ taken out to the body surface through the small incision.

JP-A-11-160942 discloses a device which comprises members for gripping the abdominal wall to fix the same, and a cylindrical member, and the spacing between the abdominal wall-gripping members is adjusted by a simple mechanism in which threads or the like, beforehand fixed to the fixing member inserted in a peritoneal cavity, are pulled up, and are fastened to the fixing member disposed outside the peritoneal cavity. In this surgical treatment instrument, when a pneumoperitoneum condition is again created, forceps can be inserted through a small incision, and can be operated thanks to the provision of two kinds of airtight members for maintaining an airtight condition when the treatment instruments is not inserted and when the treatment instrument is inserted.

By using this device, there can be performed an operation in which after a treatment, such as the abruption of those parts around the internal organ to be taken out, is sufficiently effected under a pneumoperitoneum condition, a small incision, having a size of about 3 cm to about 5 cm, is formed in that part through which the organ is to be taken out, and the organ to be treated is taken out of the body through this small incision, and the excision, extirpation and suture of the affected part are effected while the operator directly views this affected part. However, there have been encountered problems "that when the incision is opened by the threads, the threads are brought into biting engagement with that portion of the abdominal wall defining the incision, so that it is sometimes difficult to sufficiently open the incision", and "that there are provided projections for fixing a fixing member spacing-adjusting sheet, and this sheet is provided around the opened incision, so that it is sometimes difficult to take out the organ and to effect the treatment."

JP-A-10-108868 discloses a valve (capable of preventing the leakage of a pneumoperitoneum gas from the peritoneal cavity regardless of the kind of forceps to be used) and a trocar tube with the valve. This valve has a soft cylindrical member provided between two rings, and by twisting the two rings in opposite directions, respectively, forceps of different outer diameters and the arm of the operator can be inserted into the valve so as to effect a treatment within the body. By opening this valve, the internal organ can be taken out of the body, and can be treated. However, this method has a drawback that it is rather difficult to move the forceps or the like forward and backward since they are fixed by the valve in a squeezed manner. And besides, when the arm is inserted, it is sometimes difficult to maintain an airtight condition since the arm varies in thickness particularly in accordance with the forward and backward movement, and in this case it is necessary to adjust the throttling of the valve. Furthermore, the force of fixing of the device on the abdominal wall depends only on rubber elasticity of the cylindrical member, and therefore this device has a problem that it can not flexibly meet the thickness of the abdominal wall, so that the incision can not be sufficiently opened.

U.S. Pat. No. 5,480,410 discloses a device in the form of a soft enclosure having an inner surface and an open end. Spreading means for fixing the device to the abdominal wall and for maintaining an airtight condition is provided at the open end, and at least one access opening for allowing access to the interior of the enclosure is provided, and a surgical operation can be effected in the peritoneal cavity or within the enclosure. This device is not a rigid trocar as heretofore used in a laparoscopic operation and a thoracoscopic operation, but this device is made of a soft sheet material, and the spreading means, which can be deformed into a shape corresponding to the shape of an incision in the abdominal wall, is inserted through the incision, and is spread in the peritoneal cavity, and carbon dioxide gas for pneumoperitoneum purposes flows from the peritoneal cavity into the enclosure to expand this enclosure, and the spreading means maintains an airtight seal between the device and the abdominal wall. In the case where a plurality of access openings are provided in the outer peripheral surface of the enclosure, a plurality of forceps can be inserted into the enclosure, and that part beneath the incision can be observed, and the edge of the incision is protected. However, the enclosure basically has a spherical shape, and the distances to the respective access openings, provided in the outer peripheral surface, are determined and fixed when the device is set. Therefore, when one of the plurality of treatment instruments, inserted in the enclosure, is much moved, the other treatment instruments are also moved, following this treatment instrument. In addition, the incision in the abdominal wall is large relative to the treatment instrument such as forceps, and any portion of the abdominal wall does not serve as a fulcrum for the treatment instrument during the manipulation thereof, so that the manipulation of the forceps is complicated. And besides, the opening of the incision depends only on the stretchability of the sheet, and therefore there has been encountered a problem that the thickness of the abdominal wall may prevent the incision from being sufficiently opened.

U.S. Pat. No. 5,640,977 discloses a device in which this structure includes an outer sleeve, and two seal means, and this device is inserted into the peritoneal cavity through a small incision, and an airtight space is formed within the outer sleeve by the use of the two seal means. In this device, when the hand and arm of the operator is inserted into the body through the interior of this device, the internal organ can be treated in a pneumoperitoneum condition. And besides, even when the arm is withdrawn, the airtight condition in the body can be maintained if third seal means is used. However, this device has such a structure that even when the operator wants to take the internal organ out of the body so as to treat it, the sleeve portion is adhesively bonded to a drape covering the body surface of the patient. That portion, extending outwardly from the bonded portion, can not be separated, and therefore unless the drape is cut so as to once take out the whole of the device or unless the sleeve portion is cut, the organ can not be taken out of the body, and can not be treated. If the device is taken out, there is a fear that a cancer-affected tissue adheres to the abdominal wall. If the sleeve portion is cut, a pneumoperitoneum condition can not be again created after the treatment outside the body is finished, so that the observation and treatment in the peritoneal cavity can not be effected.

U.S. Pat. No. 5,813,409 discloses a device (and others) in which a sleeve is separate from an abdominal wall-fixing portion, and a ring, provided at a remote end of the sleeve, is snappingly fitted relative to a ring of the abdominal wall-fixing portion, thereby fixing the device. In this device, the sleeve can be separated from the abdominal wall-fixing portion, and therefore the sleeve portion is removed, with the abdominal wall-fixing portion remaining on the abdominal wall, and in this condition the internal organ can be taken out of the body, and can be treated. Therefore, a cancer-affected tissue will not adhere to an incision, and after the treatment is finished, the organ is returned into the body, and the sleeve is again fixed, and the observation and treatment can be effected under a pneumoperitoneum condition. However, it is difficult to snappingly fit the rings of the sleeve and abdominal wall-fixing member together over their entire periphery, and if this fitting connection is incomplete at any region, an airtight condition can not be maintained. Also in this device, when a treatment instrument such as forceps is manipulated through the sleeve, there has been encountered a drawback that the manipulation of the forceps is complicated since an incision in the abdominal wall is large relative to the treatment instrument, and any portion of the abdominal wall does not serve as a fulcrum for the treatment instrument during the manipulation thereof.

U.S. Pat. No. 5,366,478 and JP-A-2000-501978 disclose devices in which by inflating a continuous doughnut-type balloon over a region outside and inside the body, an internal cavity is closed, and an airtight condition is maintained within the peritoneal cavity when inserting and withdrawing the hand or forceps. This device is simple in structure, and can be easily assembled, and therefore the time, required for an operation, can be reduced. However, in the device of U.S. Pat. No. 5,366,478, when the organ is to be taken out of the body for treatment purposes after a pneumoperitoneum condition is canceled, the balloon must be contracted with the result that an incision is closed, and therefore there has been a drawback that an additional incision-opening instrument must be used. In both of the above devices, the balloon is inflated in the circumferential direction, so that the height of the device from the body surface increases, and therefore it is difficult to sufficiently take the organ out of the body, and besides there has been encountered a problem that forceps or the like can not be easily located at that part to be treated.

JP-A-11-99156 discloses a device in which a sleeve is fixed to the abdominal wall by ring-like members disposed respectively at the upper and lower sides of the abdominal wall, and there are provided two valves (one of which is an ordinary seal valve while the other valve is formed of an elastic thin membrane, and has a slit-like opening, and with this construction the air-tightness is enhanced when the hand is inserted and not inserted. In this device, when the hand and forceps are not inserted, the slit-like valve is expanded by a peritoneal pressure in such a manner that contact surfaces, formed by a folded portion, are pressed against each other, thereby maintaining the airtight condition. Therefore, when the valve is opened upon insertion of the hand, a force other than the resilient force of the elastic thin membrane will not be produced, and therefore the force, squeezing the arm, is very small, and in long-time use, a stress on the operator is reduced. However, this device has a drawback that when the organ is to be taken out of the body for treatment purposes after a pneumoperitoneum condition is canceled or when an affected part is to be treated while directly viewing this part through an incision, particularly the slit-like valve becomes obstructive. Also in this device, when a treatment instrument is manipulated through the sleeve, there has been encountered a drawback that the manipulation of the treatment instrument such as forceps is complicated since an incision in the abdominal wall is large relative to the treatment instrument, and any portion of the abdominal wall does not serve as a fulcrum for the treatment instrument during the manipulation thereof.

U.S. Pat. No. 5,741,298 discloses a device in which there is provided a port which firmly grips that portion of the abdominal wall, disposed around an incision, at its outer and inner sides, and is fixed thereto, and an internal cavity is closed by a lid attached to this port so that the peritoneal cavity is kept airtight when forceps are inserted and withdrawn. This device is simple in structure, and can be easily assembled, and therefore the time, required for an operation, can be reduced. However, this device can not flexibly meet the size of the incision and the thickness of the abdominal wall, and therefore there has been encountered a problem that the incision can not be sufficiently opened.

U.S. Pat. No. 5,653,705 discloses a device in which an annular member of a tapering shape, having threads, is threaded into the abdominal wall, and is fixed thereto, and a flexible envelope of the detachable type is attached thereto, and the interior of the peritoneal cavity is kept airtight when the hand or forces are inserted and withdrawn. In this device, an access port can be easily provided merely by threading the annular member into an incision, and the annular member can serve as a fulcrum for the forceps, so that the forceps can be easily manipulated. However, there has been a fear that the incision is damaged since the annular member is threaded into the incision. And besides, there has been encountered a problem that the annular member becomes bulky since the thread angle, facilitating a threading operation, is provided, and furthermore there has been a drawback that this device can not flexibly meet the thickness of the abdominal wall and the size of the incision.

DISCLOSURE OF THE INVENTION

This invention aims to overcome the above drawbacks encountered in the treatments in the conventional endoscopic operations, and an object of the invention is to provide a surgical treatment instrument in which this instrument can be set in a manner to flexibly meet various thicknesses of the abdominal wall and various sizes of an incision, and a secondary operation for opening the incision after the setting of the device can be carried out so that a treatment around the incision can be effected easily, and the height of the instrument from the body surface at the time of setting the device is low, and the mode can be easily switched between a treatment under a pneumoperitoneum condition and a treatment outside the peritoneal cavity, and in the case of effecting the treatment under the pneumoperitoneum condition, forceps can be manipulated.

Namely, according to the present invention, there are provided the following.

(1) A surgical treatment instrument comprising a tubular portion which has a first fixing member provided at a near end-side open portion thereof, and also has a second fixing member provided at a remote end-side open portion thereof; characterized in that at least two tension belts are mounted on the second fixing member; and fixing means for adjusting the length of the tension belts to position the first fixing member is provided at the first fixing member.

(2) A surgical treatment instrument according to Paragraph (1), in which the fixing means comprises belt resistance-adjusting members provided respectively in grooves formed in the first fixing member.

(3) A surgical treatment instrument according to Paragraph (2), in which the belt resistance-adjusting member includes a slit for the sliding movement of the tension belt therethrough, and means for retaining the tension belt in an airtight manner.

(4) A surgical treatment instrument according to Paragraph (3), in which the air-tightly retaining means comprises irregularities formed in the vicinity of the slit, and irregularities formed on the tension belt.

(5) A surgical treatment instrument according to Paragraph (4), in which the irregularities have a serration-like shape.

(6) A surgical treatment instrument according to Paragraph (1), in which the fixing means comprises a stopper provided at the first fixing member, a resistance portion of the tension belt, and a holder plate, and these are retainingly engaged with each other in an airtight manner.

(7) A surgical treatment instrument according to Paragraph (6), in which the air-tightly retaining means comprises irregularities formed on the stopper, and irregularities formed on the tension belt.

(8) A surgical treatment instrument according to Paragraph (7), in which the irregularities have a serration-like shape.

(9) A surgical treatment instrument according to any one of Paragraphs (1) to (8), in which the fixing means comprises an elastic member.

(10) A surgical treatment instrument according to any one of Paragraphs (3) to (9), in which the air-tightly retaining means includes means for moving one of the belt resistance-adjusting member and an irregularity portion of the tension belt to cancel the retaining engagement of the tension belt.

(11) A surgical treatment instrument according to Paragraph (10), in which the means for canceling the retaining engagement comprises a thin sheet which can be inserted between the irregularities, formed on the tension belt, and the belt resistance-adjusting member.

(12) A surgical treatment instrument according to Paragraph (10), in which the means for canceling the retaining engagement comprises a projection portion which is formed on one of the belt resistance-adjusting member and the stopper, and can move the irregularity portion in a canceling direction.

(13) A surgical treatment instrument according to any one of Paragraphs (1) to (12), in which the tubular member and the second fixing member have flexibility.

(14) A surgical treatment instrument according to any one of Paragraphs (1) to (13), in which the tension belt has a width of 10 mm to 60 mm.

(15) A surgical treatment instrument according to any one of Paragraphs (1) to (14), in which the tension belt is so constructed that it can be pulled generally horizontally.

(16) A surgical treatment instrument according to any one of Paragraphs (1) to (15), in which a converter, having an airtight seal member, mounted thereon, is combined with the first fixing member in an airtight manner.

(17) A surgical treatment instrument according to Paragraph (16), in which a plurality of airtight seal members are mounted on the converter.

(18) A surgical treatment instrument according to Paragraph (16), in which a first airtight seal member and a second airtight seal member are mounted on the converter.

(19) A surgical treatment instrument according to any one of Paragraphs (16) to (18), in which the airtight seal member is a flexible diaphragm.

(20) A surgical treatment instrument according to any one of Paragraphs (1) to (19), in which at least part of one or both of the belt resistance-adjusting member and the tension belt are made of a material whose modulus of longitudinal elasticity is 0.05 kg/mm$^2$ to 10 kg/mm$^2$.

BRIEF DESCRIPTION OF THE INVENTION

FIG. 5 is a schematic view showing a condition in which the surgical treatment instrument of the invention is retained in an incision.

FIG. 6A is a view showing one example of a tension belt of the surgical treatment instrument according to the invention, and FIG. 6B is a perspective view of another example, and FIG. 6C is a perspective view of a further example.

FIG. 7A is a cross-sectional view showing one example of ratchet grooves in the tension belt of FIGS. 6A to 6C, and FIG. 7B is a cross-sectional view showing another example.

Figure 9A:
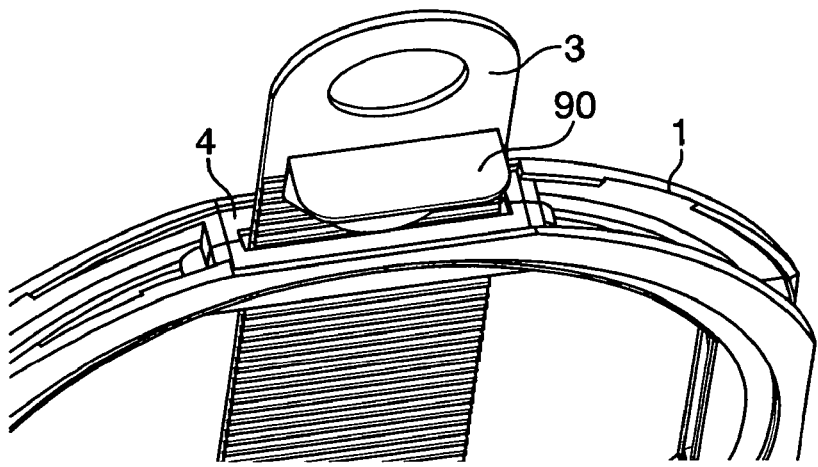
Figure 9B:
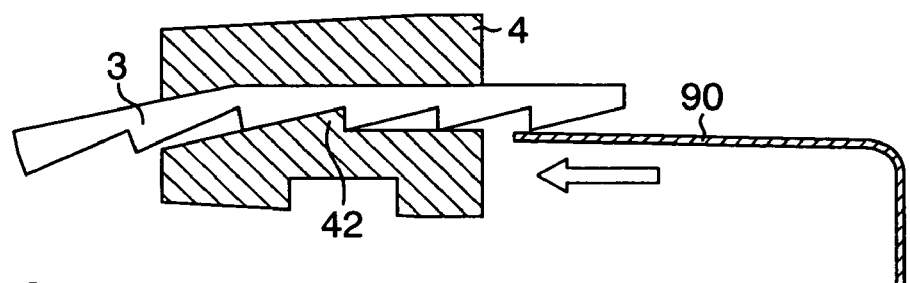
Figure 9C:
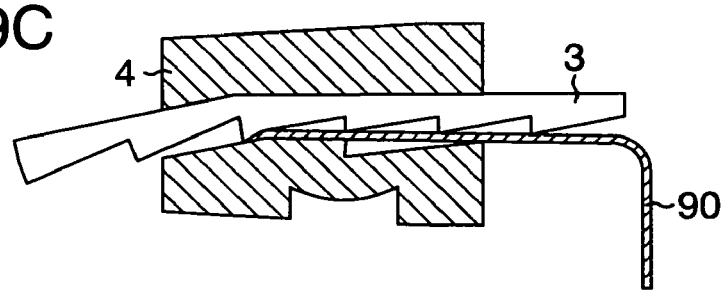

FIG. 9A is a perspective view showing the manner of canceling a retained condition by a thin sheet used in the belt resistance-adjusting member, and showing its relation with the first fixing member, and FIG. 9B is a cross-sectional view showing a condition before the thin sheet is inserted into the belt resistance-adjusting member, and FIG. 9C is a cross-sectional view showing an inserted condition of the thin sheet.

Figure 10A:
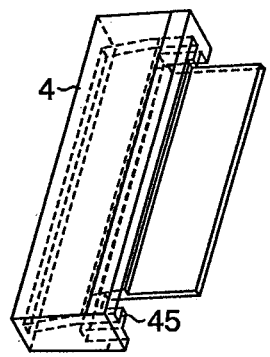
Figure 10B:
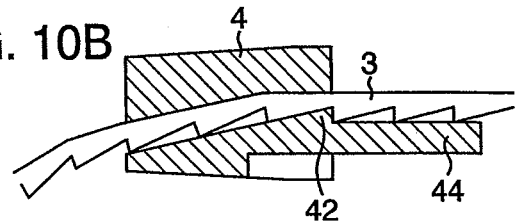
Figure 10C:
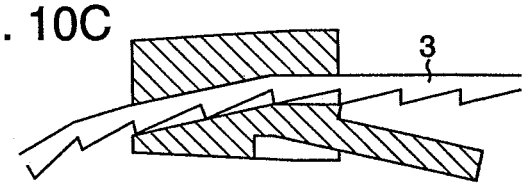

FIG. 10A is a perspective view of another example of a belt resistance-adjusting member, and FIG. 10B is a cross-sectional view showing an inserted condition of the tension belt, and FIG. 10C is a cross-sectional view showing a disengaged condition of the tension belt.

Figure 11:
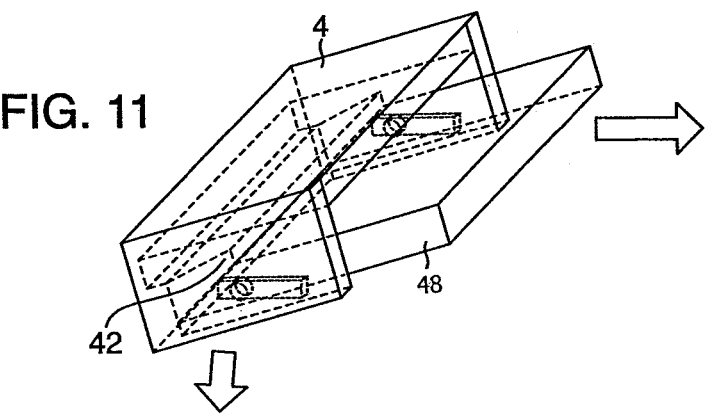

FIG. 11 is a perspective view of a further example of a belt resistance-adjusting member.

Figure 12A:
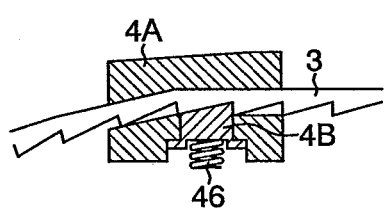
Figure 12B:
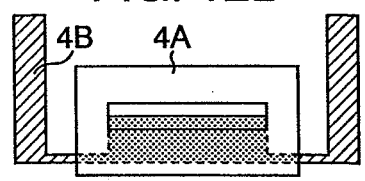
Figure 12C:
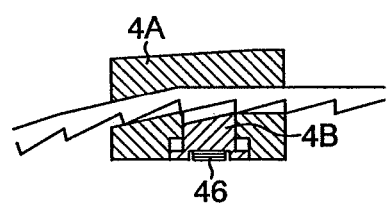
Figure 12D:
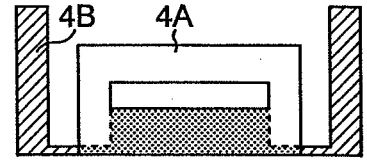

FIG. 12 is a cross-sectional view showing a further example of a belt resistance-adjusting means, showing an engaged condition of the tension belt, FIG. 12B is a cross-sectional view through a plane perpendicular to the sheet of FIG. 12A, and FIG. 12C is a cross-sectional view showing a disengaged condition of the tension belt, and FIG. 12D is a cross-sectional view through a plane perpendicular to the sheet of FIG. 12C.

Figure 13A:
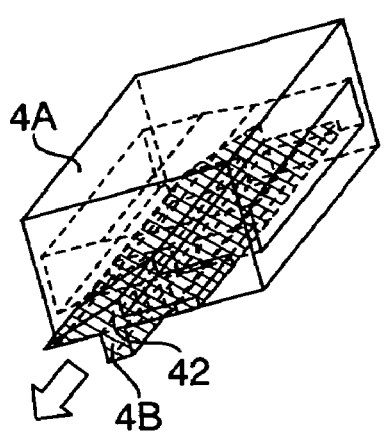
Figure 13B:
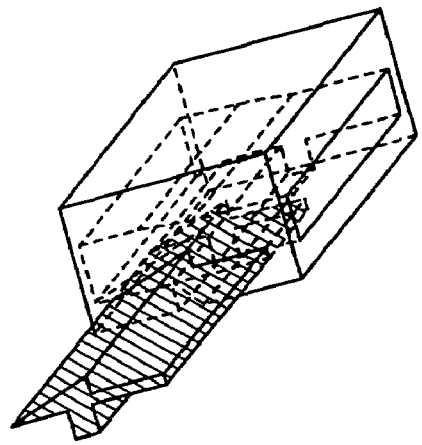

FIG. 13A is a perspective view of a further example of a belt resistance-adjusting member composed of two parts, showing a condition in which the two parts are combined together, and FIG. 13B is a perspective view showing a condition in which the two parts are separated from each other.

Figure 14A:
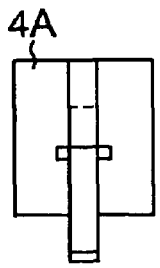
Figure 14B:
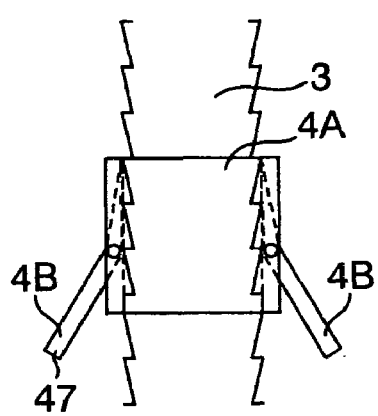
Figure 14C:
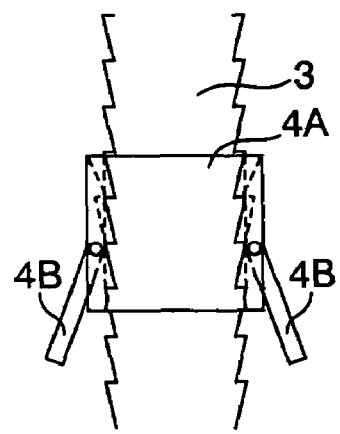

FIG. 14A is a side-elevational view of a still further example of a belt resistance-adjusting member composed of three parts, and FIG. 14B is a plan view showing an engaged condition, and FIG. 14C is a plan view showing a disengaged condition.

Figure 15A:
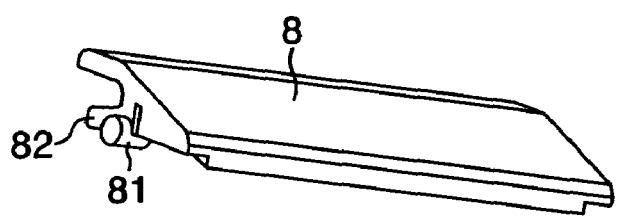
Figure 15B:
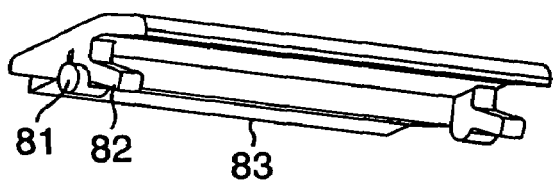

FIG. 15A is a perspective view of one example of a holder plate as seen from the upper side, and FIG. 15B is a perspective view as seen from the lower side.

Figure 16:
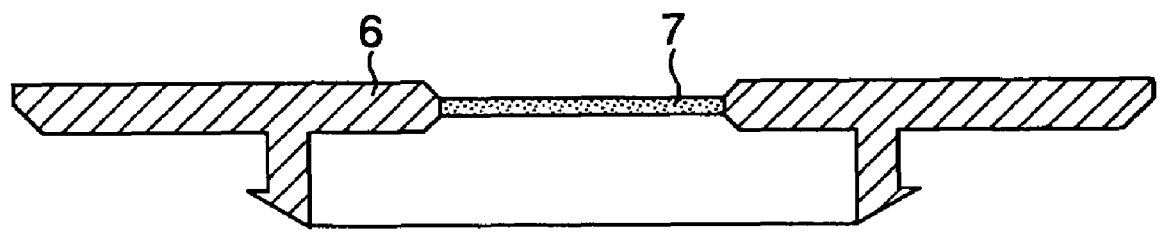

FIG. 16 is a cross-sectional view showing one embodiment of a converter.

Figure 17:
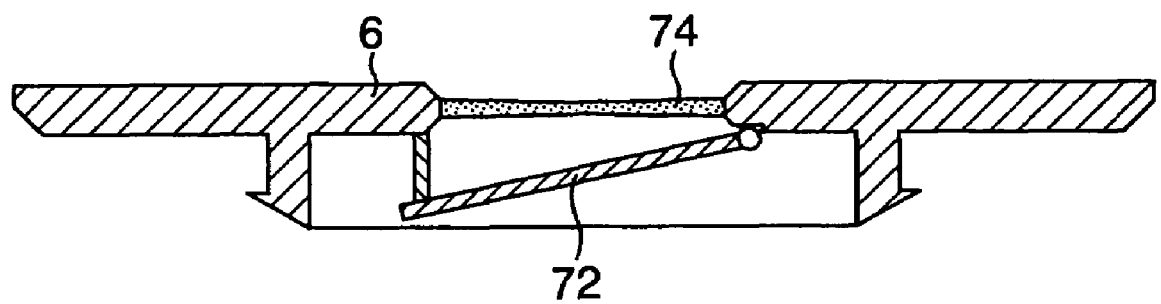

FIG. 17 is a cross-sectional view showing another embodiment of a converter.

BEST MODE FOR CARRYING OUT THE INVENTION

Figure 1A:
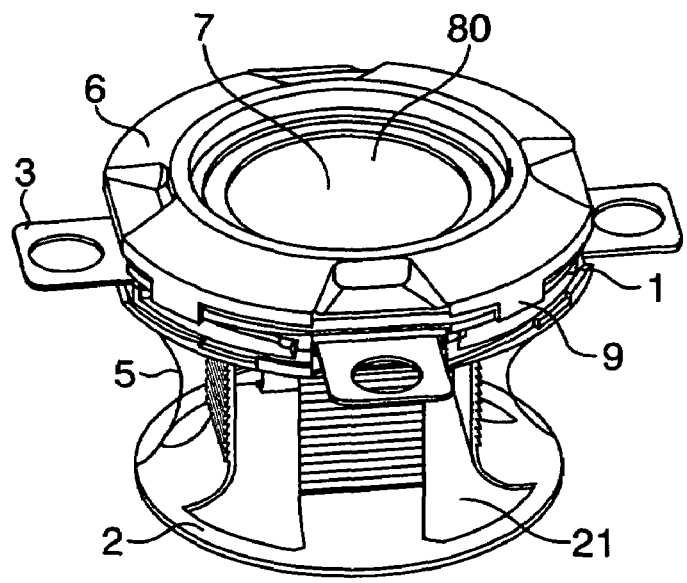
FIG. 1A is a perspective view showing the appearance of one preferred embodiment of a surgical treatment instrument of the present invention.
Figure 1B:
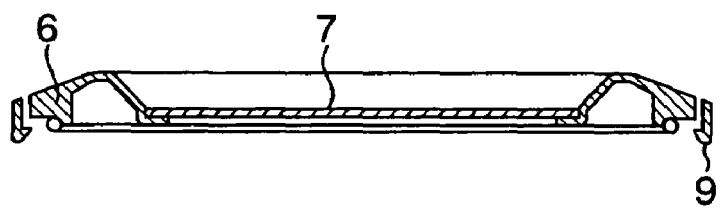
FIG. 1B is a cross-sectional view showing a converter and an airtight seal member of the surgical treatment instrument.

A surgical treatment instrument of the present invention will now be described with reference to the drawings. FIGS. 1A and 1B show the appearance of the whole. The surgical treatment instrument of the invention comprises the following parts. These parts are a first fixing member 1, second fixing member 2, tension belts 3, belt resistance-adjusting members (or stoppers provided at the first fixing member) 4, a tubular member 5, a converter 6, and an airtight seal member 7.

(Structure of Surgical Treatment Instrument)

Figure 3:
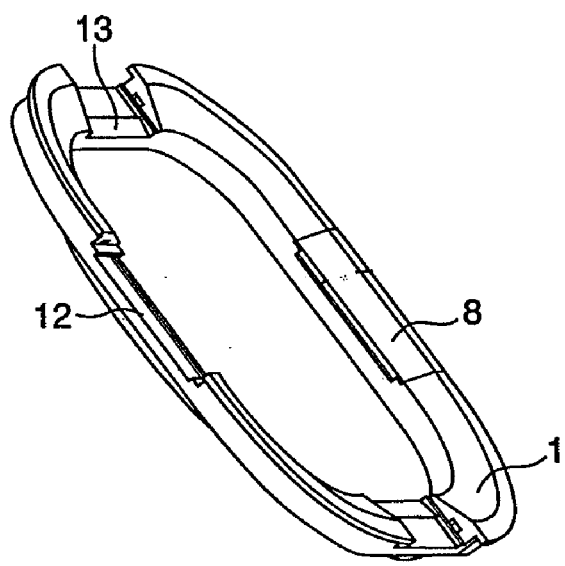
FIG. 3 is a perspective view of one example of a first fixing member.

Briefly describing the structure, the second fixing member 2 has an organ taking-out open portion 21, and is fixed to an open portion 21 of the tubular member 5. The other end of the tubular portion 5 is connected to the first fixing portion 1. An arbitrary number of tension belts 3 are provided at the second fixing member 2. With respect to means for fixing the tension belt 3 to the first fixing member 1 in an airtight manner, a groove is formed in the first fixing member 1 as shown in FIG. 3, and a holder plate 8 is fitted in this groove, and a slit 16 for the sliding movement of the tension belt 3 therethrough, is formed. Alternatively, the belt resistance-adjusting members 4 are provided in the first fixing member 1 as shown in FIG. 1, and a slit is formed in the belt resistance-adjusting member 4, and the tension belt 3 is passed through the slit in the belt resistance-adjusting member 4. The converter 6 for preventing the leakage of pneumoperitoneum gas is attached to the first fixing member 1. The airtight seal member 7 is provided at a generally central portion of the converter 6. The tubular member 5 and the tension belts 3 are larger in length than the thickness of the abdominal wall 70, and can be mounted on the abdominal wall 70 of an arbitrary thickness, and an incision can be opened by applying a tension to the tension belts 3. The converter 6 can be easily attached to the first fixing member 1, and therefore the mode can be easily shifted between the pneumoperitoneum-creating operation and the operation for taking out the organ. The airtight seal member 70 is provided at the converter 6 having a window 80, and therefore a trocar 60 or the like can be set, and a treatment, using forceps or the like, can be effected.

(First Fixing Member)

The first fixing member 1 is provided at the near end-side open portion of the tubular member 5. Usually, this first fixing member is formed by injection molding, compression molding or extrusion molding. The first fixing member is held in intimate contact with the surface of the tubular member 5, and is fixed thereto by fusion or adhesive bonding, or is fixed thereto by mechanical fastening using an O-ring or the like. The first fixing member has a generally circular shape, a polygonal shape or other shape, and is not particularly limited to any specified shape in so far as it has an organ taking-out open portion at its central portion. The fingers and hand of the operator can be inserted into this open portion, and preferably the first fixing member has such a size that when it is set on the abdomen, it is not bulky. For example, preferably, the first fixing member has a ring-like shape, that is, a generally circular shape, and its outer diameter is 50 mm to 300 mm, and its inner diameter is 30 mm to 280 mm. Preferably, the height of the first fixing member is as low as possible so that the organ can be easily drawn onto the body surface 72 through the open portion 11 and that the treatment range can be made wide when inserting a long-handled treatment instrument into the body, with the open portion 11 serving as a fulcrum. Preferably, this height is 5 mm to 50 mm. The fixing means can have the construction shown in FIG. 3, in which the groove 12 for fitting on the holder plate 8 is formed in the first fixing member 1, and the holder plate 8 is fitted in this groove, and the slit 16, in which the tension belt 3 is slidably fitted in an airtight manner, is formed. In this case, preferably, the stopper 13 for retaining the tension belt 3 is formed on the groove portion 12. The stoppers 13, shown in FIGS. 3, 4A and 4B, serve to prevent the degree of opening of the incision from decreasing, and facilitates the incision-opening operation, and relieves a stress on the operator. Alternatively, the fixing means can have the structure in which the belt resistance-adjusting members 4 are provided at the first fixing member 1. Although the belt resistance-adjusting member 4 can be provided in a groove formed in a body surface-contacting surface 10 of the first fixing member or the opposite surface thereof, preferably, cavities are formed in a side surface of the first fixing member 1 disposed perpendicular to the body surface-contacting surface 10, and the belt adjusting members 4 are provided in these cavities, respectively. With this construction, the surface, on which the converter 6 is mounted, is formed by one member, and has no joint, so that the air-tightness can be easily secured. Preferably, ribs 41 are formed at that portion of the belt resistance-adjusting-member 4 which is to be fixed, and with this construction the air-tightness is enhanced.

Preferably, the first fixing member 1 is provided with the belt resistance-adjusting members 4 for respectively pulling the tension belts 3 in a horizontal direction so that the tension belts 3 will not be obstructive when drawing the organ out of the surgical treatment instrument of the present invention for treatment purposes. The converter 6 is fitted on the first fixing member 1. Preferably, the outer edge of the first fixing member 1 is so shaped that claws 9 on the converter 6 can be engaged with this outer edge. The drawn-out organ is held in direct contact with the upper surface of the first fixing member 1, and therefore this upper surface is flat so that it will not damage the drawn-out organ. As a material of which the first fixing member 1 is made, there is used a vinyl chloride resin, a polyurethane resin, a polyamide resin, a polyethylene resin, a polypropylene resin, a polyacetal resin, an ABS resin, an SEBS resin, silicone rubber, or metal such as stainless steel.

(Second Fixing Member)

The second fixing member 2 is provided at the open portion 21 of the tubular member 5. Usually, the second fixing member is formed by injection molding, compression molding or extrusion tubing. The second fixing member is embraced by the tubular member 5, and is held in intimate contact with the tubular member 5, and is fixed thereto by fusion or adhesive bonding, or the tubular member is held in intimate contact with the surface of the second fixing member 2, and is fixed thereto by fusion or adhesive bonding. Alternatively, the fixing may be made by mechanical fastening using an O-ring or the like. In the case of effecting the excision of the large intestine with the aid of a laparoscope, preferably, the inner diameter is set to about 30 mm to 120 mm, and the outer diameter is set to about 40 mm to about 200 mm for a small incision having a size of about 20 mm to about 80 mm. It is required that the device is not bulky in the peritoneal cavity, and therefore preferably the thickness of the second fixing member is about 0.5 mm to about 10 mm. Since the ring is inserted in a bent condition into the peritoneal cavity through the incision, it is preferred that the material has a certain degree of elasticity. As the material of which the second fixing member 2 is made, there is used a vinyl chloride resin, a polyurethane resin, a polyamide resin, a polyethylene resin, a polypropylene resin, a polyacetal resin, an ABS resin, an SEBS resin, silicone rubber, or metal such as stainless steel.

(Tension Belt)

As shown in FIGS. 1A to 2B, the tension belts 3 are connected to the second fixing member 2, and are passed through the respective slits 16, each formed by the first fixing member 1 and the holder plate 8, and respective slits 43 of belt resistance-adjusting members 4. The incision is opened wide (into a shape as close to a circular shape as possible) as shown in FIG. 5, and therefore preferably the width of the tension belt 3 is not smaller than 10 mm, but if this width is excessively large, it is difficult to insert the device into the incision, and it is preferred that the width be in the range of between 10 mm and 60 mm. Preferably, the belt is in the form of a sheet having a thickness of 0.1 mm to 0.5 mm so that the height of the device from the body surface is kept to a low level. Preferably, the length of the tension belt 3 is large so as to meet various abdominal walls, but if it is too long, the tension belts are exposed to the body surface, and restrict the movement of a piercing portion of the trocar 60 or the like. Therefore, preferably, the practical length is 30 mm to 200 mm. A resistance portion 31 is provided at the tension belt 3 so that the size of the opened incision will not be decreased. The resistance portion 31 is only required to offer a resistance to the sliding movement of the tension belt 3 along the slit 43, and irregularities 42, such as projections and holes, may be merely formed at the tension belt, but preferably serration-like ratchet grooves 32 are formed as shown in FIG. 6. The depth of the ratchet grooves 32 is set to about 0.5 mm to about 2.5 mm in order to reduce the thickness of the belt 3. The ratchet grooves 32 may be formed at part of the belt 3 as shown in FIGS. 6A to 6C. When the angle of the ratchet groove 32 is made acute as shown in FIGS. 7A and 7B, the resistance, offered when opening the incision, is reduced, and this is desirable. The ratchet grooves 32 can be formed at a side surface of the belt, but preferably the ratchet grooves are formed on that surface of the belt facing away from the open portion 21 as shown in FIGS. 1A to 1C so that the organ, while drawn out, will not contact the ratchet grooves of the belt, and therefore will not be damaged. Preferably, the material has a suitable degree of flexibility, and has good sliding properties. In order to effect the smooth manipulation, preferably, the tension belt 3 has a suitable degree of hardness (Shore hardness of about A40 to about D60) so that the whole or part (that portion having the irregularities) thereof can be deformed. The tension belt is formed of a non-woven fabric or a woven sheet material, or is formed by extrusion molding, injection molding or compression molding, and the material is not particularly limited. A polyamide resin, a vinyl chloride resin, a polyurethane resin, a polyethylene resin, a polypropylene resin or a polyacetal resin can be used. A sheet, having a resin mesh or a metal mesh, is also preferred since such a sheet is less liable to be deformed.

(Belt Resistance-Adjusting Member)

Figure 1C:
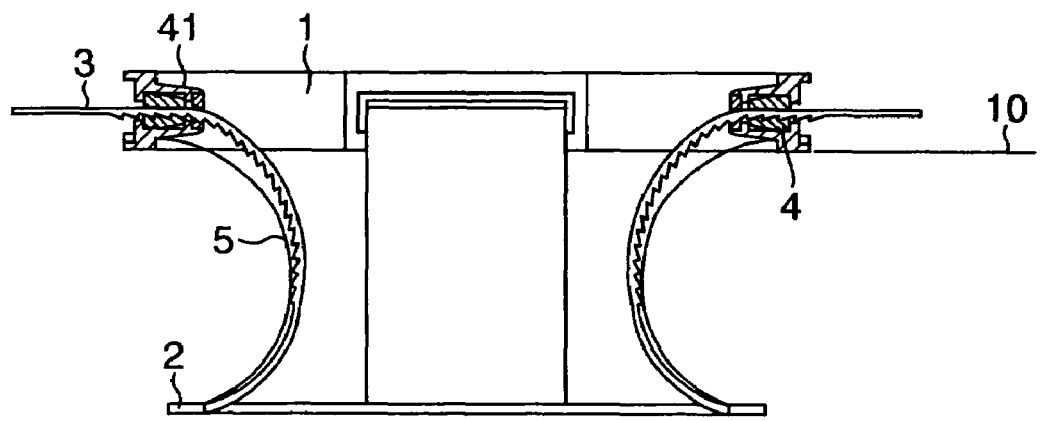
FIG. 1C is a cross-sectional view of a tubular member of the surgical treatment instrument.
Figure 8A:
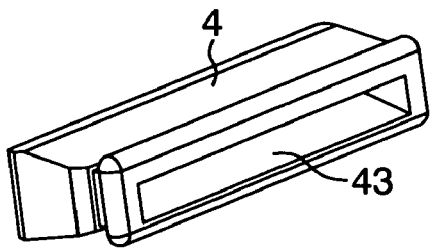
FIG. 8A is a perspective view of one example of a belt resistance-adjusting member.
Figure 8B:
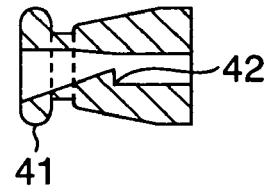
FIG. 8B is a cross-sectional view thereof.

As shown in FIG. 1C, the belt resistance-adjusting members 4 are provided at the first fixing member 1. As shown in FIGS. 8A and 8B, the belt resistance-adjusting member 4 has the slit 43 for the passage of the tension belt 3 therethrough. Preferably, the slit 43 has substantially the same cross-sectional shape as that of the tension belt 3 so as to ensure the air-tightness.

Irregularities 42, corresponding to the irregularities of the tension belt 3, are formed adjacent to the slit 43, and prevent the tension belt 3 from moving in a direction to contract the opened incision.

Preferably, the ribs 41 or recess portions are provided at the belt resistance-adjusting member 4 so as to maintain the airtight condition when this member 4 is mounted on the first fixing member 1. One example is shown in FIGS. 8A and 8B.

In order that the incision can be suitably switched between the open condition and the contracted condition, preferably, there is provided means for canceling the retained condition of the tension belt 3. For example, by inserting a thin sheet 90 between the tension belt 3 and the irregularities 42 of the belt resistance-adjusting member 4, the retaining engagement of the irregularities 42 can be canceled as shown in FIGS. 9A to 9C. The thin sheets 90 may be provided as separate members, or may be fixed to the first fixing member 1 so as to slide relative thereto. As shown in FIGS. 10A to 10C and 11, in order that irregularities 42 of the belt resistance-adjusting member 4 can be moved in a direction to cancel the retained condition, a projection portion 44 may be formed on and extend from the irregularity portion, in which case this projection portion is operated to move the irregularity portion 42. As shown in FIGS. 10A and 10B, in order that the irregularities 42 can be positively moved, preferably, notches 45 are formed respectively in those portions of the belt resistance-adjusting member 45 disposed near respectively to opposite ends of the irregularities 42. The structure, shown in FIG. 11, comprises two parts, and when the projection portion 48 of that part, including the irregularities 42, is pulled, this part is moved downwardly along guides provided at the other part. The part, including the irregularities 42, is thus moved, so that the retained condition is canceled. As shown in FIGS. 12A to 12D, the belt resistance-adjusting member 4 may be divided into two parts 4A and 4B, in which case a spring 46 is provided at the lower side of the part 4B, including irregularities, so as to move the irregularities upward and downward. As shown in FIGS. 13A and 13B, there may be provided a structure in which the belt resistance-adjusting member 4 may be divided into two parts 4A and 4B, and irregularities can be drawn in a horizontal direction. As shown in FIGS. 14A to 14C, the belt resistance-adjusting member 4 may be divided into three parts 4A, 4B and 4C, in which case irregularity portions are opened or moved by irregularities-operating portions 47. The interior of the belt resistance-adjusting member 4 may be formed into a cavity, in which case the pressure within this cavity is reduced so as to cancel the retained condition.

The irregularities for suppressing the degree of contraction of the opened incision are formed on the tension belt 3, and therefore when opening the incision, a resistance is produced. In order to effect the smooth manipulation, preferably, the belt resistance-adjusting member 4 has a suitable degree of hardness (Shore hardness of about A40 to about D60) so that the whole or part (that portion having the irregularities) thereof can be deformed. As the material, there is used a vinyl chloride resin, a polyurethane resin, a polyamide resin, a polyethylene resin, a polypropylene resin, a polyacetal resin, an ABS resin, an SEBS resin, or silicone rubber.

(Holder Plate)

Figure 4A:
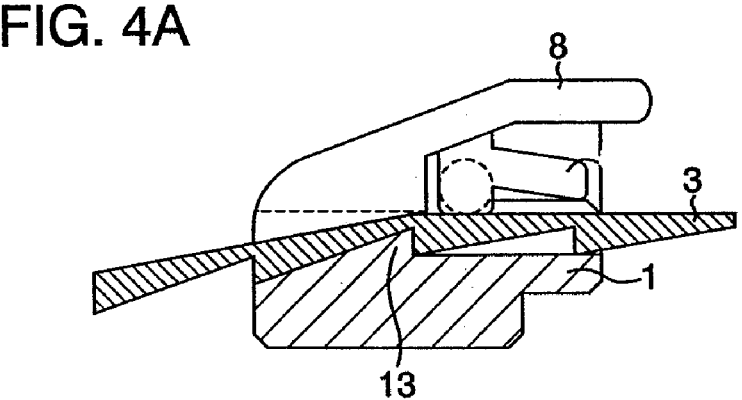
FIG. 4A is a cross-sectional view showing a groove portion of the one example of the first fixing member.
Figure 4B:
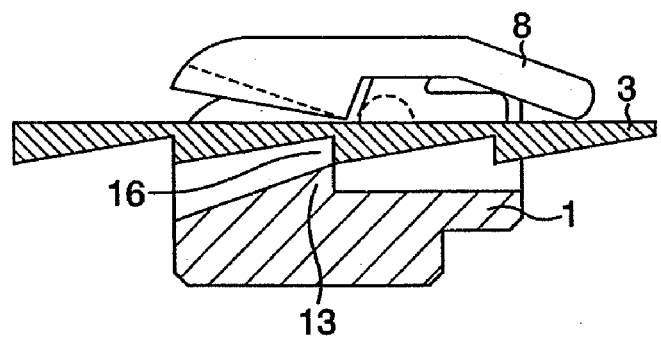
FIG. 4B is a cross-sectional view showing the disengagement of a tension belt from a stopper.

As shown in FIGS. 3, 4A and 4B, each holder plate 8 is fitted in the first fixing member 1, and forms the slit 16 in which the tension belt 3 can slide. Its shape is not particularly limited, but preferably the holder plate includes shafts 81, which are disposed near to a central axis thereof, and are fitted in the first fixing member 1, a belt holding portion 83, which holds the tension belt 3, with the shafts 81 used as fulcrums, and is held in close contact with the tension belt, and legs 82 which apply a force for pressing the belt holding portion 83 against the tension belt 3. The means for fixing the tension belt 3 comprises the irregularities 13 (formed on the first fixing member 1) for retaining engagement with the tension belt 3, and therefore in the case of using the holder plate 8, a similar mechanism to the above-mentioned mechanisms for canceling the retained condition can be applied. As the material of which the holder plate 8 is made, there is used a vinyl chloride resin, a polyurethane resin, a polyamide resin, a polyethylene resin, a polypropylene resin, a polyacetal resin, an ABS resin, a polycarbonate resin, silicone rubber, a fluorocarbon resin, or metal such as stainless steel.

(Tubular Member)

The tubular member 5 has a straight tubular shape or a generally-tapering tubular shape, and has a wall thickness of 0.05 mm to 3 mm. Usually, the tubular member is formed by inflation molding or the like, but the production method is not particularly limited. The size of the tubular member 5 varies, depending on the part to be treated and on the purpose, but in the case of effecting the excision of the large intestine with the aid of a laparoscope, preferably, the outer diameter is 30 mm to 300 mm. In use, treatment instruments, such as an endoscope and forceps, are frequently inserted and withdrawn, and therefore it is preferred to select the type of material which is not bulky, and has a suitable degree of flexibility, and will not be cut or torn when such a treatment instrument or the like strikes against the tubular member. For example, a soft vinyl chloride resin, a polyurethane resin, a polyethylene resin, a polyamide resin, a polypropylene resin, a polyester resin, an SEBS resin, silicone rubber, or natural rubber is preferably used as the material.

(Converter)

The converter 6 is mounted on the first fixing member 1, and serves to keep the interior of the peritoneal cavity airtight in a pneumoperitoneum condition. For attaching and detaching the converter, the converter may be fixed to the first fixing member 1 by convex and concave portions or by screws, but it is preferred and convenient to provide the claws 9 at the edge of the converter 6, in which case the claws are fittingly engaged with the side surface of the first fixing member 1. Usually, the converter is formed by injection molding or compression molding. In one type of converter 6, the airtight seal member 7, which is a diaphragm having no opening, is secured to this converter as shown in FIGS. 1A, 1B and 16, and a treatment instrument pierces this airtight seal member. In another type of converter, an airtight seal member is divided into two portions 72 and 74 as shown in FIG. 17, and the first airtight seal member 72 and the second airtight seal member 74 are secured to the converter. The window 80 is formed in the central portion of the converter, and the airtight seal member 7 is exposed through this window. The size of the window 80 is determined by the size of treatment instruments to be inserted, and the size of the window is suitably set to 1 mm to 80 mm. The height is suitably set to 1 mm to 40 mm so as to prevent the interference with a treatment. As the material, there is used a rigid resin, such as a vinyl chloride resin, a polyurethane resin, a polyethylene resin, a polypropylene resin, a polyacetal resin, a polycarbonate resin and a polysulfone resin, silicone rubber, natural rubber, or synthetic rubber such as NBR.

(Airtight Seal Member)

The airtight seal member 7 is provided for maintaining the airtight condition when the trocar 60 or forceps are inserted. This member is a diaphragm having no opening. Preferably, the thickness is 0.1 mm to 3 mm. If the thickness is less than 0.1 mm, the valve is liable to be deformed by the pressure of carbon dioxide gas, and if the thickness is more than 3 mm, an increased frictional resistance is produced when inserting a treatment instrument such as forceps, and as a result the insertion is difficult. Preferably, the inner diameter is set to 0.5 mm to 80 mm in view of the outer diameter of treatment instruments or others. Preferably, the airtight seal member is made of a material having a tearing strength of 5 N/mm to 100 N/mm so that an airtight condition can be maintained when a treatment instrument such as the trocar 60 is inserted. Further, it is more preferred that the material have flexibility, and for example natural rubber, silicone rubber, a vinyl chloride resin, a urethane resin or a SEBS resin is suitable.

(First Airtight Seal Member)

The first airtight seal member 72 is provided for maintaining the airtight condition when forceps or the like are not inserted. A tip of a near end may be closed by a cap or the like, or a valve member, such as a flap-type valve and a duck bill-type valve, may be provided in the interior. There may be used the type in which merely a slit is formed in a membrane of silicone rubber (elastic material) having a high tearing strength (20 kgf/cm to 50 kgf/cm). In the case of closing the end by the cap or the like, a fitting member may be provided at the near end-side inlet, in which case the cap is fitted relative to this fitting member by convex-concave fitting, or the cap may be fixed by a screw. Usually, the cap is formed by injection molding, and as its material, there is used a somewhat rigid resin, such as a vinyl chloride resin, a polyurethane resin, a polyethylene resin, a polypropylene resin, a polyacetal resin, a polycarbonate resin and a polysulfone resin, silicone rubber, natural rubber, or synthetic rubber such as NBR. With respect to the flap-type valve, a rigid molded product as contained in a trocar usually used in a laparoscopic surgical operation may be used in combination with a spring member. Alternatively, an elastic member, which is made of silicone rubber or the like, and is formed into a flap-shape, may be used. The flap-type valve will not be opened toward the outside of the body, but can be moved toward the inside of the body, and therefore when a treatment instrument or the like is not inserted, the flap is urged toward the outside of the body by a positive pressure within the body, and is closed. The flap-type valve is formed by injection molding or compression molding, and as its material, there is used a vinyl chloride resin, a polyurethane resin, a polyethylene resin, a polypropylene resin, a polyacetal resin, a polycarbonate resin and a polysulfone resin, or silicone rubber. Similarly, the duck bill-type valve is formed by injection molding or compression molding, and is mainly made of an elastic material such as silicone rubber.

(Second Airtight Seal Member)

The second airtight seal member 74 is provided for maintaining the airtight condition when forceps or the like are inserted. A seal valve, having a circular hole, or the like may be provided. The seal valve is formed by injection molding or compression molding or by processing a sheet, and is fixed to the near end-side inlet or the converter 6 by fusion or adhesive bonding. Preferably, the thickness of the seal valve is 0.1 mm to 3 mm. If the thickness is less than 0.1 mm, the valve is liable to be deformed by a pressure of carbon dioxide gas, and if the thickness is more than 3 mm, an increased frictional resistance is produced when inserting a treatment instrument such as forceps, and as a result the insertion is difficult. Preferably, the inner diameter is set to 0.5 mm to 30 mm in view of the outer diameter of treatment instruments or others. Preferably, the seal valve is made of a flexible material, and for example natural rubber, silicone rubber, a vinyl chloride resin, a urethane resin or a SEBS resin is suitable.

(Method of Use)

Next, a method of actually using the surgical treatment instrument of the present invention will be described. For effecting the excision of the large intestine with the aid of a laparoscope, first, a plurality of trocars 60 are inserted into the abdomen, and a small incision, having a size of about 3 cm to about 5 cm, is formed in that part from which the organ is expected to be taken out. The second fixing member 2 is inserted into this small incision. The tension belts 3 are pulled to open the incision.

Figure 2A:
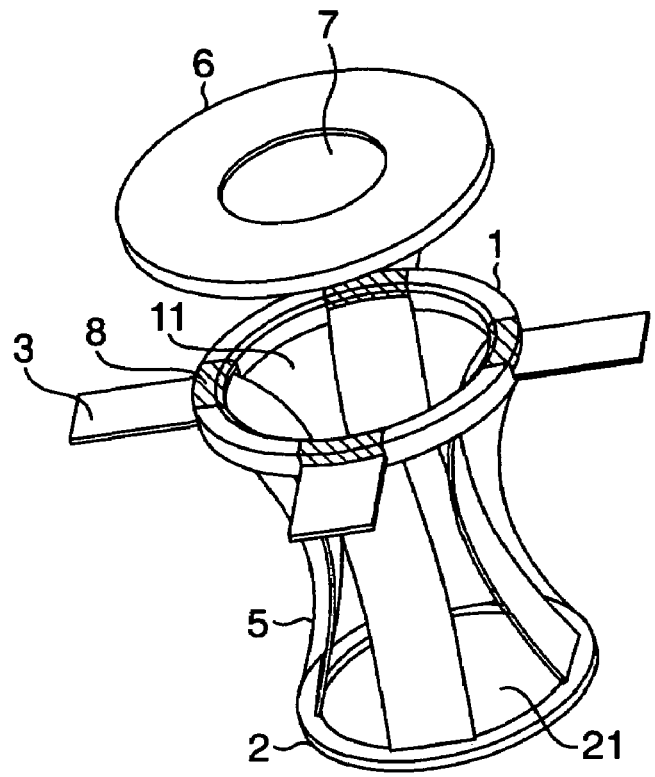
FIG. 2A is a perspective view showing the appearance of another preferred embodiment of a surgical treatment instrument of the invention.
Figure 2B:
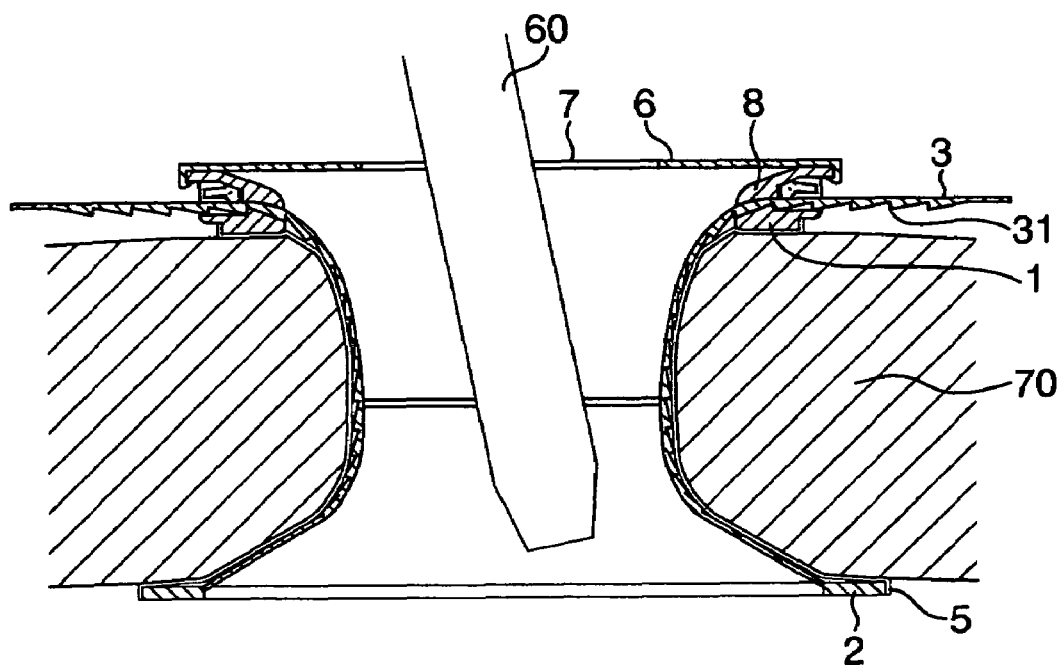
FIG. 2B is a cross-sectional view of the instrument retained in the abdominal wall, with a trocar inserted therein.

Then, the converter 6 is fixed to the first fixing member 1 in an airtight manner as shown in FIG. 2. Trocar 60 and others are caused to pierce the airtight seal member 7 of the converter 6, and a laparoscope and a treatment instrument are inserted therethrough, and treatments, such as the abruption of the large intestine, ablation of the lymph nodes and the treatment of the blood vessels, are effected under the laparoscope, and after sufficient passiveness is effected, the converter 6 is removed, and the large intestine is taken out of the body, and the excision, suture, etc., of that portion of the large intestine in the vicinity of the affected portion are effected under a directly-viewing condition, and then the large intestine is returned into the body. Then, the converter 6 is again attached to the first fixing member 1, and a pneumoperitoneum condition is again created, and the interior of the peritoneal cavity is adequately observed. If a further treatment is needed, this treatment is effected under the pneumoperitoneum condition, or the pneumoperitoneum condition is canceled, and then the converter 6 is removed, and then the treatment is effected. When the tension belts are required to be released during the treatment, this is done by the cancellation means.

In the surgical treatment instrument of the present invention, the mode can be easily switched between the treatment under the pneumoperitoneum condition and the treatment outside the peritoneal cavity merely by removing the converter 6. The airtight seal member 7 is provided at the converter 6, and therefore when the treatment under the pneumoperitoneum condition is effected, the trocar is inserted through the product of the present invention so that forcepts can be manipulated. When a cancer-affected part is taken out, the incision in the abdominal wall is protected by the tubular member 5, and there is no fear that the incision is infected with cancerous cells. The device can be fixed in such a manner that a sufficient tension is applied to the incision by the ratchet mechanisms of the tension belts 3, and the degree of opening of the incision will not be decreased. When the tension belts are required to be released, the tension belts are released, using the means for canceling the retaining engagement.

The mode can be easily switched between the treatment under the pneumoperitoneum condition and the treatment outside the peritoneal cavity during the laparoscopic operation, and that part beneath the incision can be easily treated under a directly-viewing condition, and therefore a stress on the operator is relieved, and the time, required for the operation, is shortened, and besides the incision, resulting from the operation, is smaller as compared with the ventrotomy, and the burden on the patient is smaller, and therefore the term of hospitalization of the patient after the operation is shorter, and this is very advantageous to the patient and the hospital. Furthermore, the trace of the incision after the operation is so small that it is not conspicuous, and therefore this is effective from the viewpoint of beauty.

INDUSTRIAL APPLICABILITY

The above surgical treatment instrument of the present invention not only relieves a stress on the operator, but also reduces the burden on the patient since the trace of the incision is smaller as compared with the ventrotomy, and therefore this instrument is very advantageous to the patient and the hospital.

The invention claimed is:

1. A surgical treatment instrument comprising a tubular portion which has a first fixing member provided at a near end-side open portion thereof, and also has a second fixing member provided at a remote end-side open portion thereof; characterized in that at least two tension belts are mounted on said second fixing member; and fixing means for adjusting a length of said tension belts to position said first fixing member is provided at said first fixing member, in which said fixing means comprises belt resistance-adjusting members provided respectively in grooves formed in said first fixing member, and said belt resistance-adjusting member includes a slit for the sliding movement of said tension belt therethrough, and means for retaining said tension belt in an airtight manner.

2. A surgical treatment instrument according to claim 1, in which said air-tightly retaining means comprises irregularities formed in the vicinity of said slit, and irregularities formed on said tension belt.

3. A surgical treatment instrument according to claim 2, in which said irregularities have a serration-like shape.

4. A surgical treatment instrument according to claim 1, in which said fixing means comprises a stopper provided at said first fixing member, a resistance portion of said tension belt, and a holder plate, and these are retainingly engaged with each other in an airtight manner.

5. A surgical treatment instrument according to claim 4, wherein said stopper has air-tightly retaining means comprises irregularities formed on said stopper, and irregularities formed on said tension belt.

6. A surgical treatment instrument according to claim 5, in which said irregularities have a serration-like shape.

7. A surgical treatment instrument according to claim 1, in which said fixing means comprises an elastic member.

8. A surgical treatment instrument according to claim 1, in which said air-tightly retaining means includes means for moving one of said belt resistance-adjusting member and an irregularity portion of said tension belt to cancel the retaining engagement of said tension belt.

9. A surgical treatment instrument according to claim 8, in which said means for canceling the retaining engagement comprises a thin sheet which can be inserted between the irregularities, formed on said tension belt, and said belt resistance-adjusting member.

10. A surgical treatment instrument according to claim 8, in which said means for canceling the retaining engagement comprises a projection portion which is formed on one of said belt resistance-adjusting member and said stopper, and can move the irregularity portion in a canceling direction.

11. A surgical treatment instrument according to claim 1, in which said tubular member and said second fixing member have flexibility.

12. A surgical treatment instrument according to claim 1, in which said tension belt has a width of 10 mm to 60 mm.

13. A surgical treatment instrument according to claim 1, in which said tension belt is so constructed that it can be pulled generally horizontally.

14. A surgical treatment instrument according to claim 1, in which a converter, having an airtight seal member, mounted thereon, is combined with said first fixing member in an airtight manner.

15. A surgical treatment instrument according to claim 14, in which a plurality of airtight seal members are mounted on said converter.

16. A surgical treatment instrument according to claim 14, in which a first airtight seal member and a second airtight seal member are mounted on said converter.

17. A surgical treatment instrument according to claim 14, in which said airtight seal member is a flexible diaphragm.

18. A surgical treatment instrument according to claim 1, in which at least part of one or both of said belt resistance-adjusting member and said tension belt are made of a material whose modulus of longitudinal elasticity is 0.05 kg/mm$^2$ to 10 kg/mm$^2$.

* * * * *